(12) United States Patent
Ehrhardt et al.

(10) Patent No.: US 8,613,538 B2
(45) Date of Patent: Dec. 24, 2013

(54) ILLUMINATION SYSTEM FOR ENDOSCOPY OR MICROSCOPY

(75) Inventors: Andre Ehrhardt, Wurmlingen (DE); Klaus M. Irion, Emmingen-Liptingen (DE); Uwe Martin, Spaichingen (DE); Fang Lei, Durchhausen (DE)

(73) Assignee: Karl Storz GmbH & Co. KG (DE)

( * ) Notice: Subject to any disclaimer, the term of this patent is extended or adjusted under 35 U.S.C. 154(b) by 394 days.

(21) Appl. No.: 11/844,467

(22) Filed: Aug. 24, 2007

(65) Prior Publication Data

US 2008/0055924 A1 Mar. 6, 2008

(30) Foreign Application Priority Data

Aug. 30, 2006 (DE) .......................... 10 2006 041 959

(51) Int. Cl.
*F21V 5/00* (2006.01)

(52) U.S. Cl.
USPC ............ 362/574; 362/555; 600/109; 600/179

(58) Field of Classification Search
USPC ......... 362/294, 329, 334, 335, 373, 554, 555, 362/558, 574, 580, 581; 385/31, 33, 34, 35, 385/39, 41, 42, 43, 50, 114, 119, 120, 121; 600/101, 175, 179, 180
See application file for complete search history.

(56) References Cited

U.S. PATENT DOCUMENTS 3,832,028 A * 8/1974 Kapron ............................ 385/43
4,747,660 A * 5/1988 Nishioka et al. ................. 385/31
4,790,618 A * 12/1988 Abe ................................. 385/93
5,099,399 A * 3/1992 Miller et al. ................... 362/580
5,191,629 A * 3/1993 Kaiser ............................. 385/90
5,353,294 A * 10/1994 Shigeno ..................... 372/43.01
5,631,991 A * 5/1997 Cohen et al. ..................... 385/93

(Continued)

FOREIGN PATENT DOCUMENTS

JP 2005347223 A 12/2005
WO 2005035059 A1 4/2005

OTHER PUBLICATIONS

European Search Report, Dec. 14, 2007, 6 Pages.
German Search Report, Apr. 10, 2007, 4 pages.

(Continued)

*Primary Examiner* — Hargobind S Sawhney
(74) *Attorney, Agent, or Firm* — St. Onge Steward Johnston & Reens LLC

(57) ABSTRACT

An illumination system for producing light and for launching the light into a proximal end of an optical cable of an observation apparatus for endoscopy or microscopy has a light source having at least one LED. In addition, the illumination system has an optical light guiding element between the light source and the proximal end of the optical cable for introducing the light emitted by the light source into the proximal end of the optical cable, wherein a first end region of the optical light guiding element on a side facing the light source has a smaller cross-sectional area than a second end region of the optical light guiding element on a side facing the proximal end of the optical cable. Furthermore, the illumination system has a cooling apparatus which has at least one cooling body and which is thermally conductively connected to the light source in order to remove heat produced by the light source from the illumination system. The cooling body is arranged completely on a side of the light source which is remote from the optical light guiding element.

16 Claims, 5 Drawing Sheets

(56) References Cited

U.S. PATENT DOCUMENTS

| | | | | |
|---|---|---|---|---|
| 5,631,992 A * | 5/1997 | Takahashi et al. | | 385/94 |
| 5,778,127 A * | 7/1998 | Gilliland et al. | | 385/92 |
| 5,803,575 A * | 9/1998 | Ansems et al. | | 362/554 |
| 6,200,134 B1 * | 3/2001 | Kovac et al. | | 433/29 |
| 6,402,347 B1 * | 6/2002 | Maas et al. | | 362/294 |
| 6,542,669 B1 * | 4/2003 | Hanley et al. | | 385/38 |
| 6,638,063 B2 * | 10/2003 | Otsuka | | 433/29 |
| 6,692,251 B1 * | 2/2004 | Logan et al. | | 433/29 |
| 6,692,432 B1 * | 2/2004 | Yarush et al. | | 600/179 |
| 6,741,777 B2 * | 5/2004 | Jewell et al. | | 385/49 |
| 6,796,939 B1 * | 9/2004 | Hirata et al. | | 600/179 |
| 6,918,762 B2 * | 7/2005 | Gill et al. | | 433/29 |
| 6,945,674 B2 * | 9/2005 | Yoneda et al. | | 362/294 |
| 7,029,277 B2 * | 4/2006 | Gofman et al. | | 433/29 |
| 7,062,129 B2 * | 6/2006 | Archer | | 385/39 |
| 7,101,072 B2 * | 9/2006 | Takada et al. | | 362/573 |
| 7,182,597 B2 * | 2/2007 | Gill et al. | | 433/29 |
| 7,217,022 B2 * | 5/2007 | Ruffin | | 362/554 |
| 7,360,934 B2 * | 4/2008 | Sakurada | | 362/553 |
| 7,364,335 B2 * | 4/2008 | Muehlemann et al. | | 362/555 |
| 7,390,129 B2 * | 6/2008 | Yonekubo et al. | | 385/93 |
| 7,403,680 B2 * | 7/2008 | Simbal | | 385/31 |
| 7,410,306 B2 * | 8/2008 | Wipiejewski | | 385/88 |
| 7,654,750 B2 * | 2/2010 | Brenner et al. | | 385/89 |
| 7,798,692 B2 * | 9/2010 | Krupa et al. | | 362/558 |
| 2004/0127961 A1 | 7/2004 | Whitehurst | | |
| 2004/0260365 A1 | 12/2004 | Groseth et al. | | |
| 2005/0201100 A1 | 9/2005 | Cassarley et al. | | 362/317 |
| 2006/0171693 A1 | 8/2006 | Todd et al. | | 396/17 |
| 2007/0018181 A1 * | 1/2007 | Steen et al. | | 257/98 |
| 2007/0195548 A1 * | 8/2007 | Wang | | 362/555 |

OTHER PUBLICATIONS

European Examination Report; Application No. 07 016 792.9; Nov. 4, 2010; 4 pages.

* cited by examiner

ILLUMINATION SYSTEM FOR ENDOSCOPY OR MICROSCOPY

CROSS-REFERENCE TO RELATED APPLICATION

The present application claims priority of German patent application No. 2006 041 959.6 filed on Aug. 30, 2006.

BACKGROUND OF THE INVENTION

The invention generally relates to illumination systems for producing light. The invention particularly relates to an illumination system for producing light and for launching the light into a proximal end of an optical cable of an observation apparatus for endoscopy or microscopy. More specifically, the invention relates to an illumination system of the aforementioned kind having a cooling apparatus for removing heat produced by a light source of the illumination system.

A thermal conductive connection is to be understood within the context of the present invention to mean direct thermal contact or indirect thermal contact between the cooling apparatus, i.e. the cooling body, and the light source which (contact) can be used to effectively remove the heat produced by the light source.

An illumination system of this kind is used in endoscopy or microscopy in order to illuminate a region which is to be observed. The illumination system is generally connected by means of an optical cable to an endoscope or a microscope in which the light is guided by means of light guiding optics in the form of optical elements and/or light guides. The illumination system therefore needs to provide a sufficient light output in order to be able to illuminate the region to be observed in optimum fashion. The high light output means that the light source produces a large quantity of heat. This quantity of heat produced by the light source needs to be removed so as not to impair the performance of the light source.

US 2005/0201100 A1 discloses an illumination system which has LED as light source. Arranged between the LED and an optical cable, which is used to route the light to the region which is to be observed, is an optical light guiding element in the form of a lens. The lens is used to launch the light into the optical cable so that losses in intensity at the launch point between the LED and the optical cable are reduced. A first end region of the lens on the side of the lens which faces the LED has a smaller cross-sectional area than a second end region of the lens which faces the optical cable.

In addition, the known illumination system has a cooling apparatus which has a cylindrical cooling body which is at a distance from the LED and which at least partially surrounds the LED and the lens. The heat produced by the LED is removed to the cooling body by the LED holder, by a cooling plate which is arranged on a side of the LED which is remote from the lens, or by a reflector in which the LED is accommodated.

A drawback of this illumination system is that the heat produced by the LED is removed by means of small components, i.e. the LED holder, the cooling plate and the reflector, with which the lens is in direct or indirect thermal contact. The large amount of heat produced by the LED means that these small components heat up, and therefore the lens heats up, to a large extent. As a result, thermal stability of the lens is not assured, which means that its optical properties (refractive index or the like) can change. The impaired operation of the lens can result in a reduction in the light output from the illumination system.

It is also found to be disadvantageous that the cooling body is arranged at a physical distance from the light source. Heat is conducted from the light source to the cooling body via the aforementioned small components, which are bottlenecks for the conduction of heat, so that consequently the quantity of heat produced by the LED is delivered to the cooling body poorly. This inadequate cooling impairs the operation of the illumination system.

Another drawback of the illumination system is its design, in which the LED and the lens are accommodated in the cylindrical cooling body. If the LED needs to be replaced on account of its limited life or the lens needs to be replaced as a result of damage, these repairs are found to be particularly time consuming, since both components are not freely accessible but rather are arranged in the cooling body.

SUMMARY OF THE INVENTION

It is therefore an object of the present invention to provide a remedy for this and to develop an illumination system of the type mentioned at the outset such that it allows efficient cooling of the light source without impairing the optical light guiding element.

According to an aspect of the invention, an illumination system for producing light and for launching the light into a proximal end of an optical cable of an observation apparatus is provided, the system comprising a light source having at least one light emitting diode (LED) for producing and emitting light, an optical light guiding element arranged between the light source and the proximal end of the optical cable for introducing the light emitted by the light source into the proximal end of the optical cable, the optical light guiding element having a first end region on a side facing the light source and a second end region facing the proximal end of the optical cable, the first end region having a cross-sectional area smaller than a cross-sectional area of the second end region. The system further comprises a cooling apparatus having at least one cooling body and being thermally conductively connected to the light source in order to remove heat produced by the light source from the illumination system, the cooling body being arranged completely on a side of the light source which is remote from the optical light guiding element.

Arranging the cooling body on a side of the light source which is remote from the optical light guiding element allows the heat produced by the light source to be removed outside a region which contains the optical light guiding element. This advantageously results in no thermal interaction between the cooling apparatus and the optical light guiding element, which means that the latter's optical properties (refractive index or the like) do not change even during operation of the illumination system. In this way, a constant light output is maintained for the light emitted by the light source and launched into the optical cable.

Another advantage of arranging the cooling body completely on a side of the light source which is remote from the optical light guiding element is that it is possible to replace the light source and the optical light guiding element particularly easily and expeditiously. Since the light source and the optical light guiding element are freely accessible and not accommodated in the cooling body, no additional time is required for removing and fitting the cooling body during the repair.

In one preferred refinement, the light source, the optical light guiding element, the proximal end of the optical cable and the cooling body are arranged in a common housing.

This measure has the advantage that the illumination system has a compact design which is easy to implement technically. In addition, this refinement of the illumination system is found to be advantageous during operation, since the housing of the illumination system comprises only one housing part, not a plurality of housing parts, which means that when the illumination system is started up, for example, no difficulties can arise which result from assembling a plurality of housing parts.

In another preferred refinement, the cooling body is connected in thermally conductive fashion, particularly in directly thermally conductive fashion, to the housing.

A thermally conductive connection between the cooling body and the housing is to be understood to mean direct thermal contact or indirect thermal contact between the two components. In the case of indirect thermal contact, for example, additional components which conduct heat are arranged between the cooling body and the housing.

This measure has the advantage that the heat is not only delivered into the interior of the illumination system via the cooling body but rather is likewise removed to the outside via the housing. This means that no buildup of heat arises within the illumination system, so that the operation of the illumination system is not impaired.

In another preferred refinement, the cooling body is configured as passive cooling, particularly in the form of a heatpipe.

This measure has the advantage that the illumination system is cooled by means of heat convection. This type of cooling is sufficiently well known from the prior art and also avoids additional components, such as lines, for routing a cooling liquid or a gas to the light source. In addition, passive cooling reduces the risk of a short, which may arise particularly as a result of contact between the cooling liquid or the gas and the electrical supply lines for the light source or the light source itself.

The embodiment of the cooling body as a heatpipe advantageously allows a very efficient cooling mechanism which is known from the prior art. In this context, the cooling body is configured as a sealed hollow body made of a thermally conductive material, for example aluminium, on whose inner side there is arranged a wick-like material with a capillary action, and which is also filled with a liquid under inherent pressure or possibly under reduced pressure. When heat is supplied to the surface of the hollow body, the liquid inside the hollow body begins to boil and vaporizes as it absorbs heat energy. This vapour is distributed in the interior of the hollow body and condenses to release heat at a colder point on the inner wall of the hollow body. The wick-like material with a capillary action in turn absorbs the condensed liquid and transports it back to a point in the heatpipe at which heat is supplied. The heatpipe therefore provides a closed cooling circuit whose liquid or condensed vapour cannot enter the inside of the housing and come into contact with the current-carrying components of the illumination system.

In another preferred refinement, the optical light guiding element is electrically insulating.

This measure has the advantage that a flow of current cannot be transferred from the light source to which voltage can be applied to the optical light guiding element, i.e. to the optical cable and the housing. This increases the safety of the person who is using the illumination system during medical examinations, for example. In addition, the optical cable cannot heat up as a result of the supplied current, which means that its operation is not impaired as a result of heating.

In another preferred refinement, the optical light guiding element is configured as a glass body, particularly as a lens.

This measure advantageously allows an embodiment of the optical light guiding element which is sufficiently well known from the prior art in order to launch the light emitted by the light source into the optical cable. In addition, a glass body is particularly inexpensive to manufacture and ensures electrical insulation between the light source and the optical cable on account of its low electrical conductivity. The lens may be in the form of a Compound Elliptical Concentrator (CEC) or in the form of a Compound Hyperbolic Concentrator (CHC), for example.

In another alternative refinement, the optical light guiding element is constructed from optical fibres.

This measure likewise provides an advantageous refinement of the optical light guiding element. The use of optical fibres avoids a complex surface shape of the glass body for guiding light, since the beams of light which are emitted by the light source are routed through the optical light guiding element by the orientation of the optical fibres. In addition, the use of optical fibres allows use to be made of the entire surface, facing the front of the optical cable, of the second end region of the optical light guiding element, in order to launch the beams of light into the optical cable.

In another preferred refinement, the optical light guiding element tapers in direction to the light source.

This measure has the advantage that the cross-sectional area of the first end region of the optical light guiding element can be optimally matched to the cross-sectional area of the light source and therefore allows the light to be efficiently launched into the optical light guiding element. In addition, the beams of light in the optical light guiding element are expanded on account of the optical light guiding element being designed to expand towards the optical cable, so that the front of the optical cable, which usually has a greater diameter than the light source, is lit in optimum fashion.

The optical light guiding element may have a constriction between its two end regions.

In another preferred refinement, the optical light guiding element is configured as a truncated cone.

This measure allows an advantageously simple design for the tapering optical light guiding element which is simple to implement technically. If, by way of example, a reflective layer is additionally put onto the outer face of the optical light guiding element in order to reduce a loss of intensity in the light in the optical light guiding element, this can be done particularly easily, since the outer face of the optical light guiding element is smooth any without any curvature.

In another preferred refinement, the optical light guiding element is configured in pear-shaped form, with the optical fibres in the first end region of the optical light guiding element being directed towards the light source.

This measure has the advantage that the beams of light which are emitted radially outward by the approximately punctiform light source (LED) can be launched into the optical light guiding element in optimum fashion by means of the optical fibres which point towards the light source, so that a loss of light intensity between the light source and the optical light guiding element is reduced.

In another preferred refinement, a numerical aperture of the first end region of the optical light guiding element is larger than a numerical aperture of the second end region of the optical light guiding element.

This measure has the advantage that when it has passed through the optical light guiding element the divergent light emitted by the light source is converted into a less divergent beam of light which can then be launched into the optical cable without any significant loss of the intensity.

In another preferred refinement, the optical light guiding element is arranged at a slight distance from the light source.

This measure has the advantage that this arrangement of the optical light guiding element at a slight distance from the light source provides further electrical insulation between the optical light guiding element and the light source. This prevents damage to the optical light guiding element and also reduces any risk to the person using the illumination system.

In another preferred refinement, the first end region of the optical light guiding element is at least partially glued onto the light source.

This measure has the advantage that when the light is launched no loss of light intensity arises between the light source and the optical light guiding element. Furthermore, additional scatter of the beams of light emitted by the light source on molecules of air situated between the light source and the optical light guiding element can be reduced, which scatter would produce even greater divergence in the beams of light. If the light source is arranged at a slight distance from the optical light guiding element, this distance can be filled with the adhesive.

In another preferred refinement, the illumination system has an electrically insulating holder element in which the optical light guiding element is arranged.

This measure advantageously allows further insulation between the light source to which voltage can be applied and the optical light guiding element and the housing of the illumination system, so that risk to people is likewise reduced.

In another preferred refinement, the illumination system has a socket through which the proximal end of the optical cable is introduced into the illumination system.

This measure has the advantage that it provides a technically easily implemented opportunity to introduce the optical cable into the illumination system in reproducible fashion and to put it into the position favourable to launching the light.

Further advantages and features can be found in the description which follows and in the appended drawing.

It goes without saying that the features mentioned above and the features which are yet to be explained below can be used not just in the indicated combinations but also in other combinations or on their own without departing from the scope of the present invention.

BRIEF DESCRIPTION OF THE DRAWINGS

The invention is described and explained in more detail below using a few selected exemplary embodiments in connection with the accompanying drawing, in which.

DETAILED DESCRIPTION OF PREFERRED EXEMPLARY EMBODIMENTS

Figure 1:
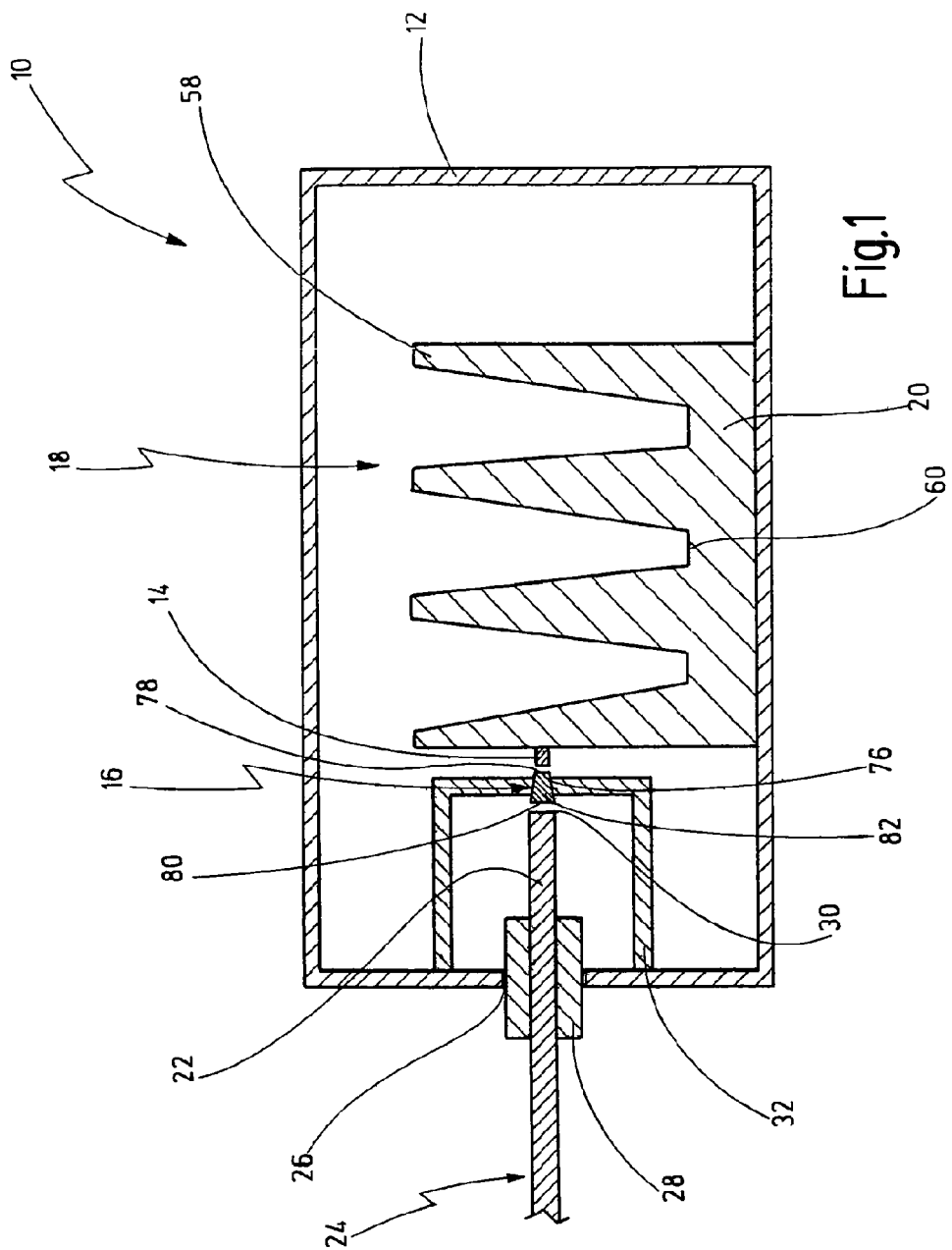
FIG. 1 shows a schematic illustration of an illumination system.
Figure 2:
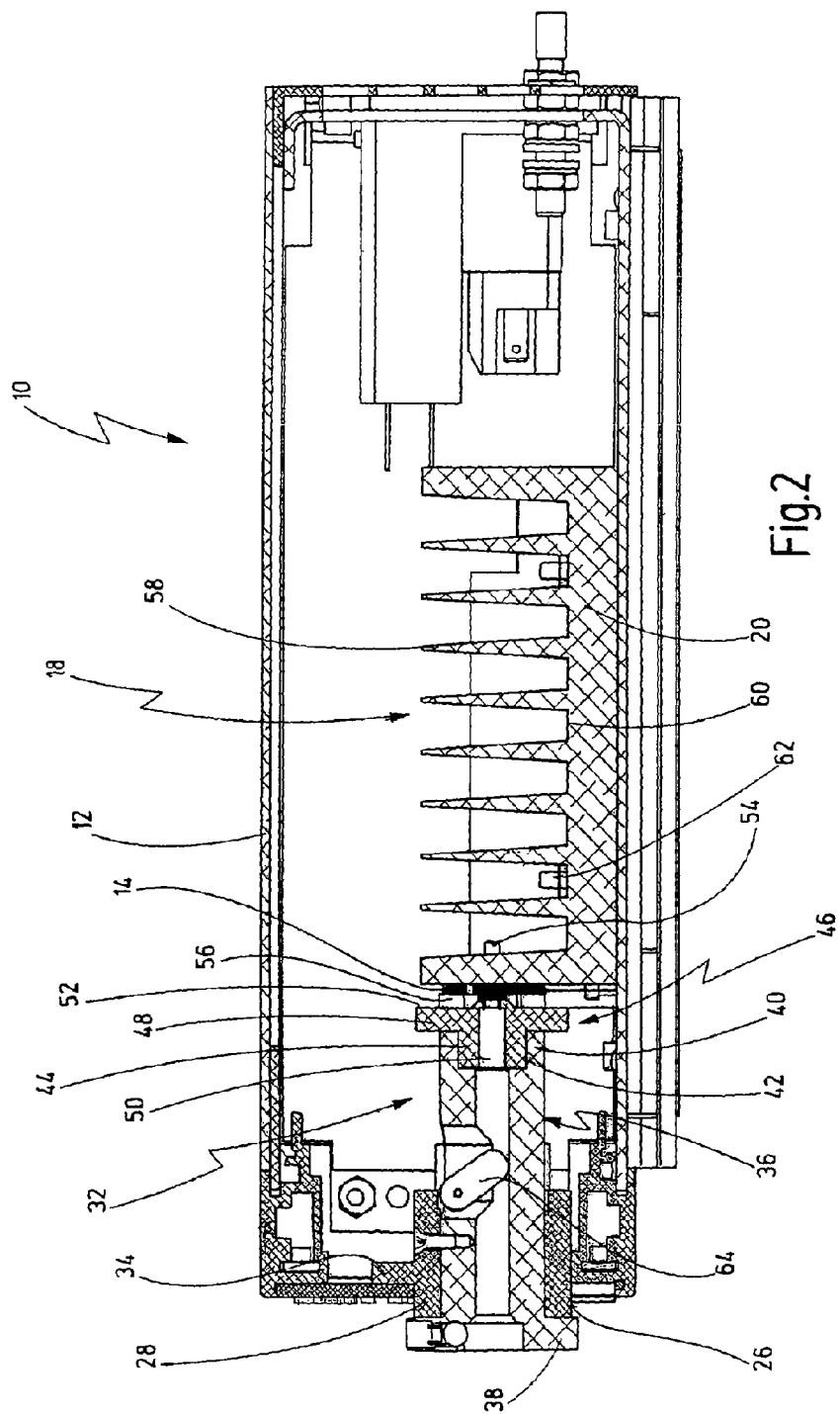
FIG. 2 shows a detailed illustration of the illumination system in FIG. 1.

FIGS. 1 and 2 show an illumination system provided with the general reference symbol 10, wherein identical, similar or comparable components have the same reference symbol. Further details of the illumination system 10 are shown in FIG. 3 and FIGS. 4A-4D.

The illumination system 10 is used in endoscopy or microscopy to illuminate a region which is to be observed, for example.

The illumination system 10 has a housing 12 which contains a light source 14, an optical light guiding element 16 and a cooling apparatus 18.

The light source 14 is thermally conductively connected to the cooling apparatus 18, i.e. to a thermally conductive cooling body 20, where a thermally conductive connection is intended to be understood to mean direct or indirect thermal coupling of the two components. The cooling body 20 is arranged on a side of the light source 14 which is remote from the optical light guiding element 16, the light source 14 preferably being arranged directly on the cooling body 20, so that heat produced by the light source 14 is delivered directly to the cooling body 20 and can be removed by it. The cooling body 20 is also thermally conductively connected to the housing 12, so that the heat absorbed from the cooling body 20 can be removed to the housing 12. The dimensions of the cooling body 20 are large in comparison with those of the light source 14, which means that the cooling body 20 can efficiently absorb and remove the heat produced by the light source 14.

A proximal end 22 of an optical cable 24 which is connected to an endoscope (cf. FIG. 5), for example, can be introduced into the housing 12 by a socket 28 arranged in an opening 26 in the housing 12, or the proximal end 22 of the optical cable 24 may be permanently arranged in the illumination system 10 when it has been introduced. The proximal end 22 of the optical cable 24 comes to rest in the housing 12 such that a front 30 of the proximal end 22 of the optical cable 24 points in the direction of the light source 14 and is arranged at a short distance therefrom. Arranged between the front 30 of the proximal end 22 of the optical cable 24 and the light source 14 is the electrically insulating optical light guiding element 16, which is held in the housing 12 by an electrically insulating holder element 32.

As FIG. 2 shows, the opening 26 contains the socket 28 in order to introduce the proximal end 22 of the optical cable 24 into the housing 12 of the illumination system 10. The socket 28 is in the form of a short, cylindrical hollow tube with an annular widened portion 34 which is used to attach the socket 28 to the housing 12. The socket 28 contains a holder 36, which is likewise in the form of a cylindrical hollow tube, using the matching shapes. A first end region 38 of the holder 36, which is arranged outside the socket 28, i.e. outside the housing 12, and which introduces the proximal end 22 of the optical cable 24 into the housing 12, is widened in annular fashion. A second end region 40 of the holder 36 has a comprehensive depression 42 whose diameter is designed to be larger than an internal diameter of the holder 36. The depression 42 accommodates a first section 44 of a disc 46 using the matching shapes. A second annular section 48 of the disc 46 has a larger external diameter than the first section 44 of the disc 46 and than the holder 36, so that it projects beyond the holder 36. The disc 46 also has a cylindrical passage 50 whose internal diameter roughly corresponds to an internal diameter of the holder 36. The passage 50 in the disc 46 contains the optical light guiding element 14 (not shown).

The holder element 32 shown in FIG. 1 is formed by the holder 36 and the disc 46 in this case, both components being manufactured from an electrically insulating material, for example plastic.

The light source 14 is arranged at a distance from a front 52 of the second section 48 of the disc 46 and is rearwardly connected to the cooling body 20 by a screw 54, the screw 54 being able to be in the form of an M3 thread, for example. For stabilization purposes and to maintain a distance between the light source 14 and the second section 48 of the disc 46, extensively distributed bolts 56 pass through the second end region 40 of the holder 36, the second section 48 of the disc 46, the light source 14 and the cooling apparatus 16.

The cooling apparatus 18 is preferably in the form of passive cooling and works by means of heat convection between the light source 14 and the cooling body 20. To remove the heat produced by the light source 14, the cooling apparatus has the thermally conductive cooling body 20, which is arranged on the side of the light source 14 which is remote from the optical light guiding element 16. To increase the removal of heat, the cooling body 20 also has protruding ribs 58 which taper towards their free ends. The ribs 58 are at a distance from one another such that interfaces 60 contain screws 62 which attach the cooling body 20 to the housing 12.

The heat produced by the light source 14 is delivered to the cooling body 20 by means of the direct contact between the light source 14 and the cooling body 20 and also by means of the screw 54. The heat supplied to the cooling body 20 is distributed along the cooling body 20 and is delivered to the housing 12 from the latter.

The cooling apparatus 18 may likewise be in the form of a heatpipe, to which end the cooling body 20 is in the form of a sealed hollow body made of a thermally conductive material, for example aluminium. Arranged on an inner side of the hollow body is a wick-like material with a capillary action. The hollow body is also filled with a liquid under inherent pressure or possibly under a reduced pressure. When a surface of the heatpipe is supplied with heat from the light source 14, the liquid inside the heatpipe begins to boil and vaporizes as it absorbs heat energy. This vapour is distributed in the hollow body and condenses to release heat at a colder point on an inner wall of the heatpipe. The wick-like material with a capillary action in turn absorbs the condensed liquid and transports it back to a point in the heatpipe at which heat is supplied. The heatpipe therefore forms a closed cooling circuit which can be used to efficiently cool the illumination system 10.

The proximal end 22 of the optical cable 24 can be retained in the holder 36 by a fixing mechanism. To this end, a locking lever 64 is arranged on the holder 36 and can be used to clamp the proximal end 22 of the optical cable 24, for example.

Figure 3:
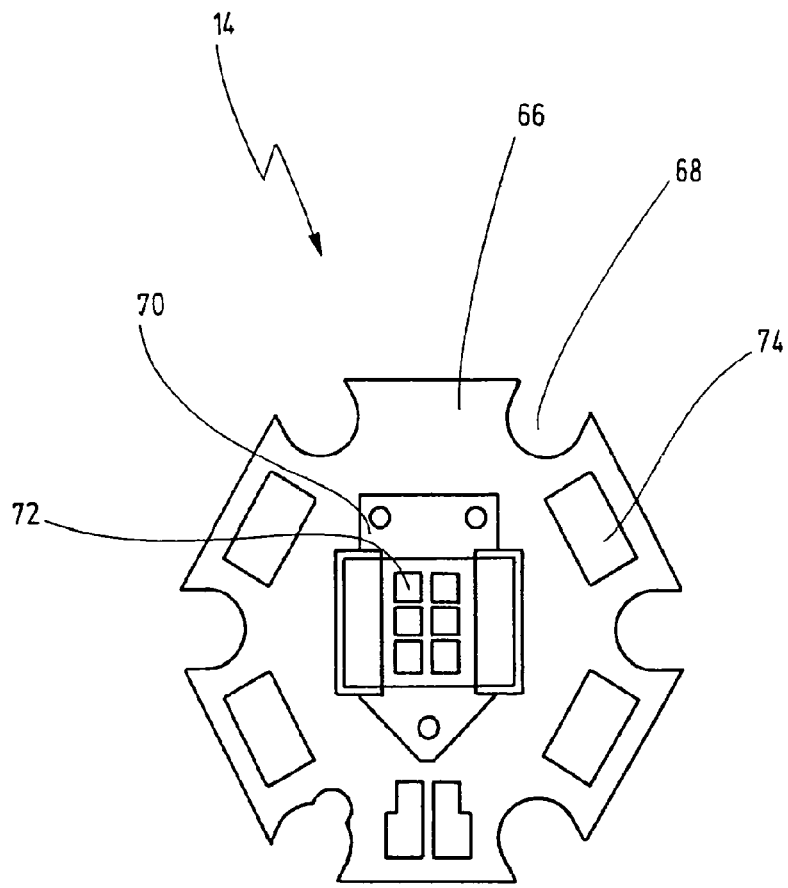
FIG. 3 shows a light source for the illumination system in FIG. 2 on its own.

The light source 14 is in the form of a conventional OSTAR® Lighting light source from the company Osram, for example, as shown in FIG. 3. This light source has a flat, hexagonal aluminium metal body 66 at whose respective corners a respective cutout 68 is formed. The bolts 56 can be pushed through these cutouts 68. Arranged on the metal body 66 are six GaN-LEDs 72 mounted on a ceramic plate 70, which emit light in the white spectral range. The LEDs 72 can have electrical contact made with them by means of appropriate contacts 74 on the metal body 66.

FIGS. 4A-4D show various embodiments of the optical light guiding element 16. The optical light guiding element 16 has a first end region 76 whose cross-sectional area 78 is designed to be smaller than a cross-sectional area 80 of a second end region 82 of the optical light guiding element 16. The optical light guiding element 16 is accommodated in the illumination system 10 such that the first end region 76 points towards the light source 16, while the second end region 82 is directed towards the front 30 of the proximal end 22 of the optical cable 24 (see FIG. 1).

In addition, the optical light guiding element 16 may be in truncated cone form (see FIGS. 4A, 4B) or else in pear-shaped form (see FIGS. 4C, 4D), with an arbitrary cross-sectional area of the optical light guiding element 16 between the two end regions 76, 82 being parabolic, elliptical, hyperbolic, circular or conical. Preferably, the optical light guiding element 16 is in the form of a Compound Elliptical Concentrator (CED) or in the form of a Compound Hyperbolic Concentrator (CHC).

The optical light guiding element 16 tapers from the second end region 82 to the first end region 76. In addition, the optical light guiding element 16 can have a constriction 84 between the first end region 76 and the second end region 82 (see FIG. 4C). A cross-sectional area 86 in the region of the constriction 84 is designed to be smaller than the cross-sectional area 80 of the second end region 82 and smaller or larger than the cross-sectional area 78 of the first end region 70.

In addition, the first end region 76 of the optical light guiding element 16 may have a depression 88 which can at least partially accommodate the LED 72. The depression 88 may be in the form of a surface of a spherical segment (with radius R, see FIG. 4B), in cylindrical form or else in cuboid form (see FIG. 4D), for example, for the purpose of at least partially accommodating the LED 72, wherein a cross-sectional area 90 of the depression 88 may be designed to be smaller than the cross-sectional area 78 of the first end region 76 of the optical light guiding element 16. The second end region 82 of the optical light guiding element 16 may be curved in the direction of the proximal end 22 of the optical cable 24 (see FIG. 4b), it being able to have a honeycombed or smooth shape, for example.

Figure 4A:
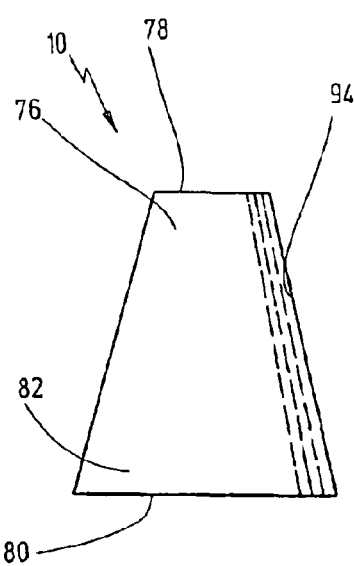
FIGS. 4A-4D shows various exemplary embodiments of an optical light guiding element in FIG. 1.
Figure 4B:
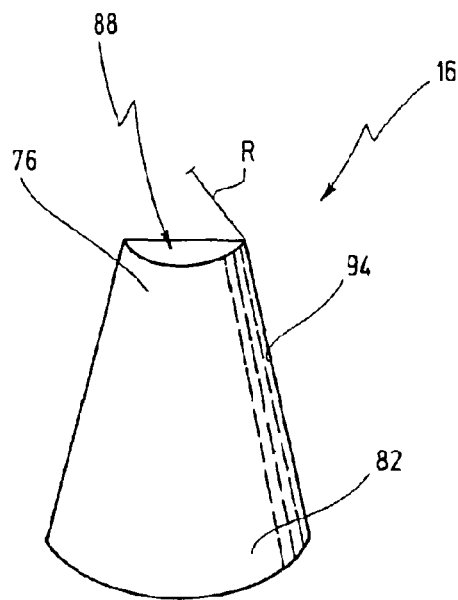
Figure 4C:
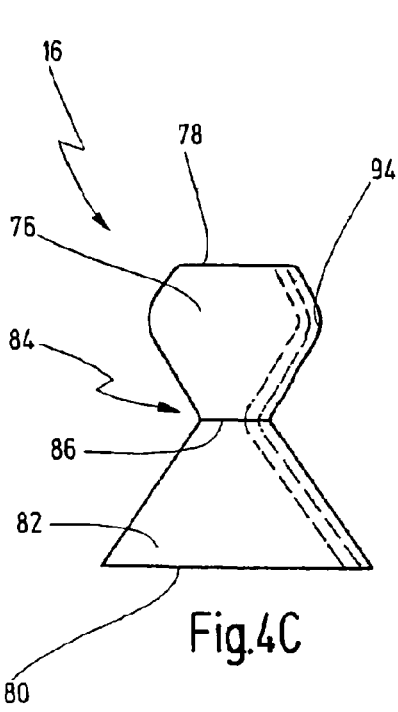
Figure 4D:
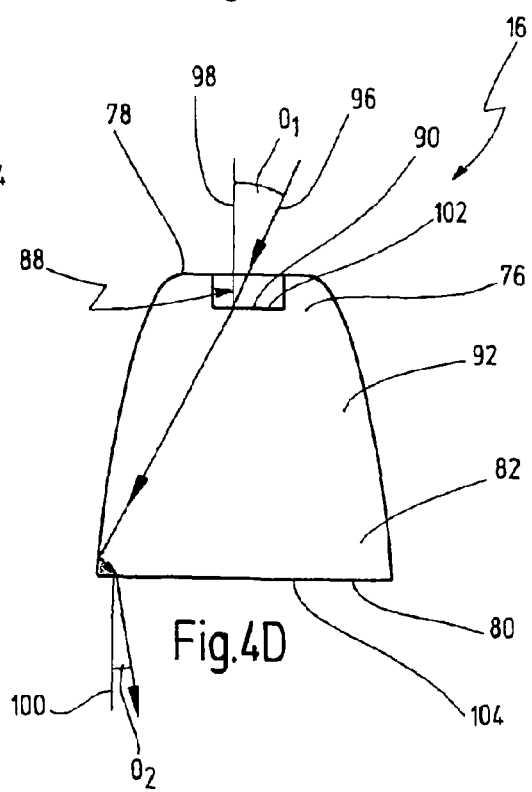

The optical light guiding element 16 is preferably in the form of a glass body 92, particularly in the form of a lens (see FIG. 4D). In one alternative embodiment, the optical light guiding element 16 is constructed from the optical fibres 94. The optical fibres 94 may be directed towards the light source 14 in the first end region 76 of the optical light guiding element 16. In addition, the optical fibres 94 may taper towards the first end region 76. As FIG. 4D shows, a numerical aperture of the first end region 76 of the optical light guiding element 16 is designed to be larger than a numerical aperture of the second end region 82 of the optical light guiding element 16, so that an angle of entrance $\Theta_1$ for a beam of light 96 which is emitted by the light source 14 is larger than an angle of emergence $\Theta_2$. In this context, $\Theta_1$, $\Theta_2$ is an intermediate angle between a normal 98, 100 and a surface 102, 104 of the first end region 76 or of the second end region 82.

Since it is made of glass or of glass fibres, the optical light guiding element 16 is electrically insulating, which means that no currents can break through from the light source 14 to which voltage can be applied to the optical light guiding element 16 and the proximal end 22 of the optical cable 24 or the housing 12.

The optical light guiding element 16 may be arranged at a slight distance from the light source 14, the distance preferably being able to be 2/10 mm to 4/10 mm. The optical light guiding element 16 may likewise be at least partially glued onto the light source 14 by means of a transmitting adhesive in order to reduce light scatter on molecules of air between the light source 14 and the optical light guiding element 16. In this context, the distance between the light source and the optical light guiding element may be filled with the adhesive.

Figure 5:
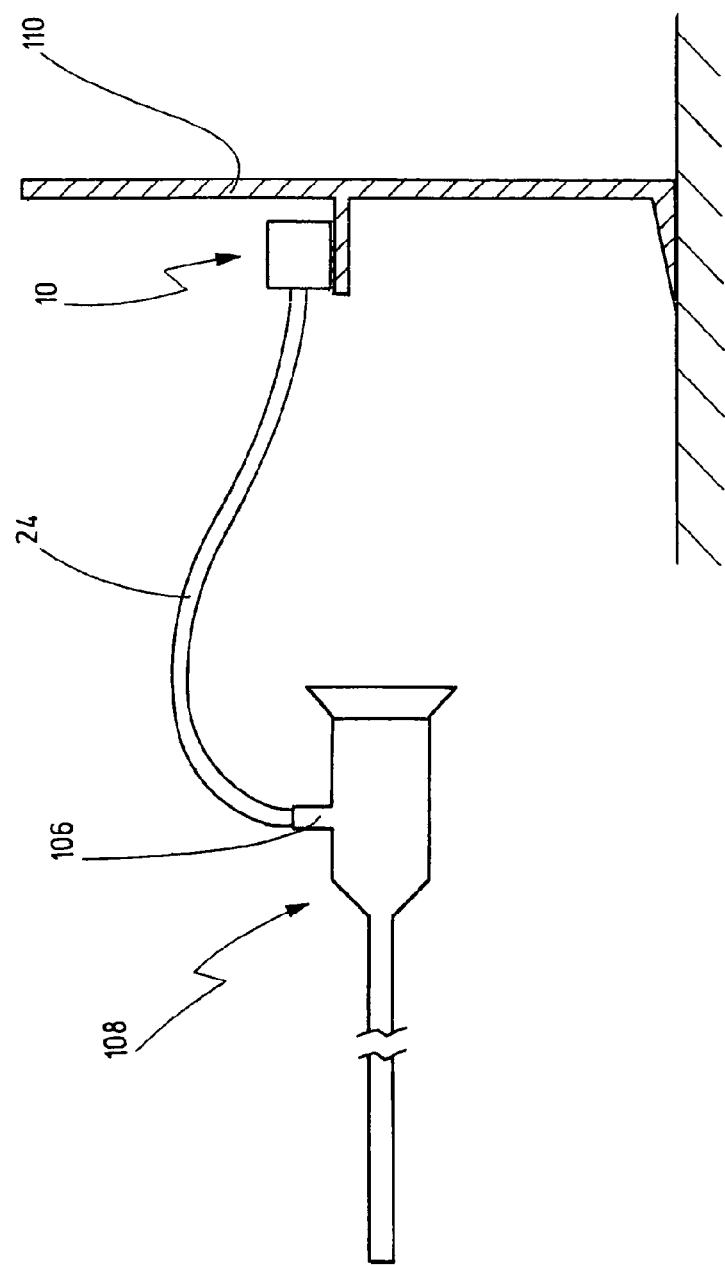
FIG. 5 shows the illumination system in FIG. 1 while it is connected to an endoscope.

As FIG. 5 shows, the illumination system 10 is connected to a connection 106 on the endoscope 108, for example, by means of the optical cable 24 during operation in order to route the light emitted by the light source 14 via the optical cable 24 and light guiding optics accommodated in the endoscope 108 (not shown) to the region which is to be illuminated. During operation, the illumination system 10 may be arranged on a mount 110, for example a rack.

What is claimed is:

1. An endoscopic system comprising:
   an endoscope;
   an optical cable; and
   an illumination system for producing light and for launching the light into a proximal end of the optical cable connecting the illumination system to the endoscope, the illumination including:
   a light source having at least one light emitting diode (LED) for producing and emitting light, said light source having at least one light emitting end face,
   an optical light guiding element arranged between said light source and said proximal end of said optical cable for introducing the light emitted by said light source into said proximal end of said optical cable, said optical light guiding element having a first end region on a side facing said light source and a second end region facing said proximal end of said optical cable, said first end region having a cross-sectional area smaller than a cross-sectional area of said second end region,
   said light guiding element being configured as a solid body, said solid body having a plane end face facing said light source, said plane end face being arranged at a slight distance from said at least one light emitting end face of said light source, said slight distance being an air-gap,
   said light guiding element having a second end face opposite to said end face facing said light source, said second end face being plane and arranged at a slight distance from said proximal end of said optical cable,
   an electrically insulating holder element, said optical light guiding element being arranged in said electrically insulating holder element, and
   a cooling apparatus having at least one cooling body and being thermally conductively connected to said light source in order to remove heat produced by said light source from said illumination system, said cooling body arranged completely on a backside of said light source which faces away from said optical light guiding element.

2. The endoscopic system of claim 1, wherein said light source, said optical light guiding element, said proximal end of said optical cable and said cooling body are arranged in a common housing.

3. The endoscopic system of claim 2, wherein said cooling body is connected in thermally conductive fashion to said housing.

4. The endoscopic system of claim 3, wherein said cooling body is directly connected to said housing.

5. The endoscopic system of claim 1, wherein said cooling body is configured as passive cooling.

6. The endoscopic system of claim 5, wherein said cooling body is configured as a heatpipe.

7. The endoscopic system of claim 1, wherein said optical light guiding element is electrically insulating.

8. The endoscopic system of claim 1, wherein said optical light guiding element is configured as a glass body.

9. The endoscopic system of claim 8, wherein said optical light guiding element is configured as a lens.

10. The endoscopic system of claim 1, wherein said optical light guiding element is constructed from optical fibers.

11. The endoscopic system of claim 1, wherein said optical light guiding element tapers in direction to said light source.

12. The endoscopic system of claim 1, wherein said optical light guiding element is configured as a truncated cone.

13. The endoscopic system of claim 10, wherein said light guide element is configured in pear-shaped form with said optical fibers in said first end region of said optical light guiding element being directed towards said light source.

14. The endoscopic system of claim 1, wherein a numerical aperture of said first end region of said optical light guiding element is larger than a numerical aperture of said second end region of said optical light guide.

15. The endoscopic system of claim 1, wherein said illumination system has a socket through which said proximal end of said optical cable is introduced into said illumination system.

16. An endoscopic system comprising:
    an endoscope;
    an optical cable; and
    an illumination system for producing light and for launching the light into a proximal end of the optical cable connecting the illumination system to the endoscope, the illumination system including:
    a light source having at least one light emitting diode (LED) for producing and emitting light,
    an optical light guiding element arranged between said light source and said proximal end of said optical cable for introducing the light emitted by said light source into said proximal end of said optical cable, said optical light guiding element having a first end region on a side facing said light source and a second end region facing said proximal end of said optical cable, said first end region having a cross-sectional area smaller than a cross-sectional area of said second end region,
    said light guiding element being configured as a solid body, said solid body having a plane end face facing said light source, said light guiding element having a second end face opposite to said end face facing said light source, said second end face being plane and arranged at a slight distance from said proximal end of said optical cable,
    an electrically insulating holder element, said optical light guiding element being arranged in said electrically insulating holder element, and
    a cooling apparatus having at least one cooling body and being thermally conductively connected to said light source in order to remove heat produced by said light source from said illumination system, said cooling body arranged completely on a backside of said light source which faces away from said optical light guiding element.

* * * * *